(12) United States Patent
Cao et al.

(10) Patent No.: US 7,331,959 B2
(45) Date of Patent: Feb. 19, 2008

(54) CATHETER ELECTRODE AND RAIL SYSTEM FOR CARDIAC ABLATION

(75) Inventors: Hong Cao, Shakopee, MN (US); John Avi Roop, Crystal, MN (US); Kedar Ravindra Belhe, Minnetonka, MN (US); Saurav Paul, Minneapolis, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 419 days.

(21) Appl. No.: 10/857,421

(22) Filed: May 27, 2004

(65) Prior Publication Data

US 2005/0267461 A1  Dec. 1, 2005

(51) Int. Cl.
    *A61B 18/14* (2006.01)
(52) U.S. Cl. ............................................. 606/41
(58) Field of Classification Search ............. 606/41
    See application file for complete search history.

(56) References Cited

U.S. PATENT DOCUMENTS

| 5,263,493 | A | | 11/1993 | Avitall |
| 5,482,037 | A | * | 1/1996 | Borghi ..................... 600/381 |
| 5,487,385 | A | | 1/1996 | Avitall |
| 5,542,928 | A | | 8/1996 | Evans et al. |
| 5,582,609 | A | | 12/1996 | Swanson et al. |
| 5,687,723 | A | | 11/1997 | Avitall |
| 5,800,482 | A | | 9/1998 | Pomeranz et al. |
| 5,836,947 | A | | 11/1998 | Fleischman et al. |
| 5,842,984 | A | | 12/1998 | Avitall |
| 5,885,278 | A | | 3/1999 | Fleischman |
| 5,895,417 | A | * | 4/1999 | Pomeranz et al. ........... 606/41 |
| 5,910,129 | A | | 6/1999 | Koblish et al. |
| 5,921,924 | A | | 7/1999 | Avitall |
| 5,971,983 | A | | 10/1999 | Lesh |
| 6,048,329 | A | | 4/2000 | Thompson et al. |
| 6,064,902 | A | | 5/2000 | Haissaguerre et al. |
| 6,071,274 | A | | 6/2000 | Thompson et al. |
| 6,071,279 | A | | 6/2000 | Whayne et al. |
| 6,071,282 | A | | 6/2000 | Fleischman |
| 6,076,012 | A | | 6/2000 | Swanson et al. |
| 6,119,041 | A | | 9/2000 | Pomeranz et al. |
| 6,120,500 | A | | 9/2000 | Bednarek et al. |
| 6,138,043 | A | | 10/2000 | Avitall |
| 6,152,920 | A | * | 11/2000 | Thompson et al. ........... 606/41 |
| 6,203,525 | B1 | | 3/2001 | Whayne et al. |
| 6,214,002 | B1 | | 4/2001 | Fleischman et al. |
| 6,217,528 | B1 | | 4/2001 | Koblish et al. |
| 6,314,962 | B1 | | 11/2001 | Vaska et al. |
| 6,314,963 | B1 | | 11/2001 | Vaska et al. |
| 6,330,473 | B1 | | 12/2001 | Swanson et al. |
| 6,332,880 | B1 | * | 12/2001 | Yang et al. ................. 604/528 |
| 6,402,746 | B1 | | 6/2002 | Whayne et al. |
| 6,413,234 | B1 | * | 7/2002 | Thompson et al. ......... 604/95.04 |
| 6,447,507 | B1 | | 9/2002 | Bednarek et al. |
| 6,454,758 | B1 | | 9/2002 | Thompson et al. |

\* cited by examiner

*Primary Examiner*—Lee S. Cohen
(74) *Attorney, Agent, or Firm*—Heimbecher & Assoc., LLC

(57) ABSTRACT

The instant invention is directed toward an ablation catheter and sheath incorporating wire rail system. The catheter may have a combination of rigid and flexible components to orient an ablation electrode at the distal tip toward the target tissue. The wire rail acts to guide an ablation tip along the tissue to aid in the formation of spot or continuous linear lesions on a trabecular surface, e.g., in the right atrium along the isthmus between the ostium of the inferior vena cava and the tricuspid valve.

15 Claims, 12 Drawing Sheets

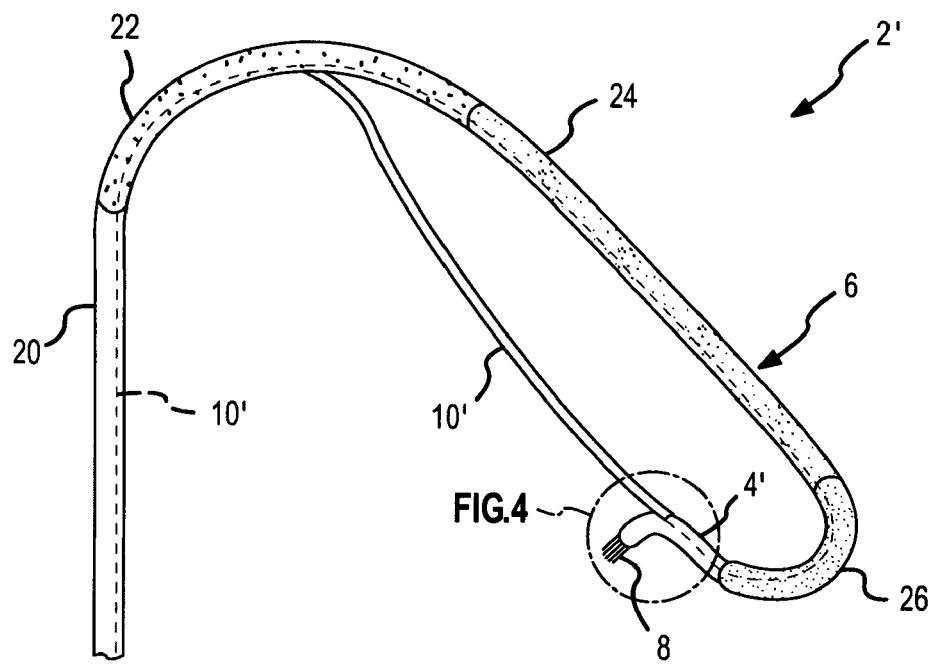
FIG.3
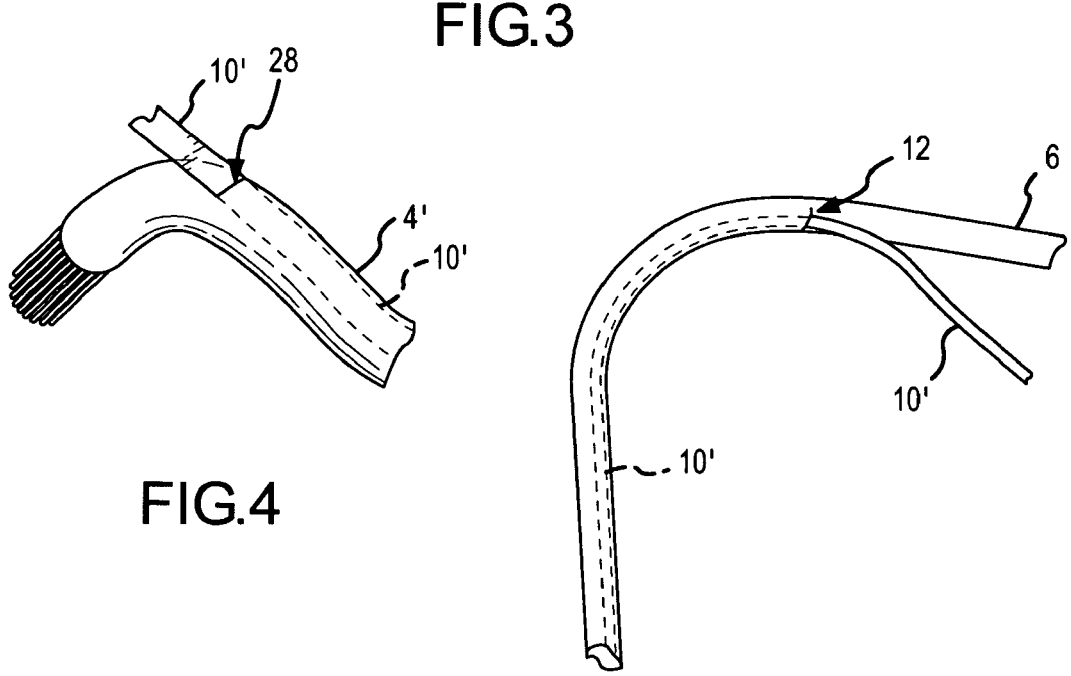
FIG.4
FIG.5

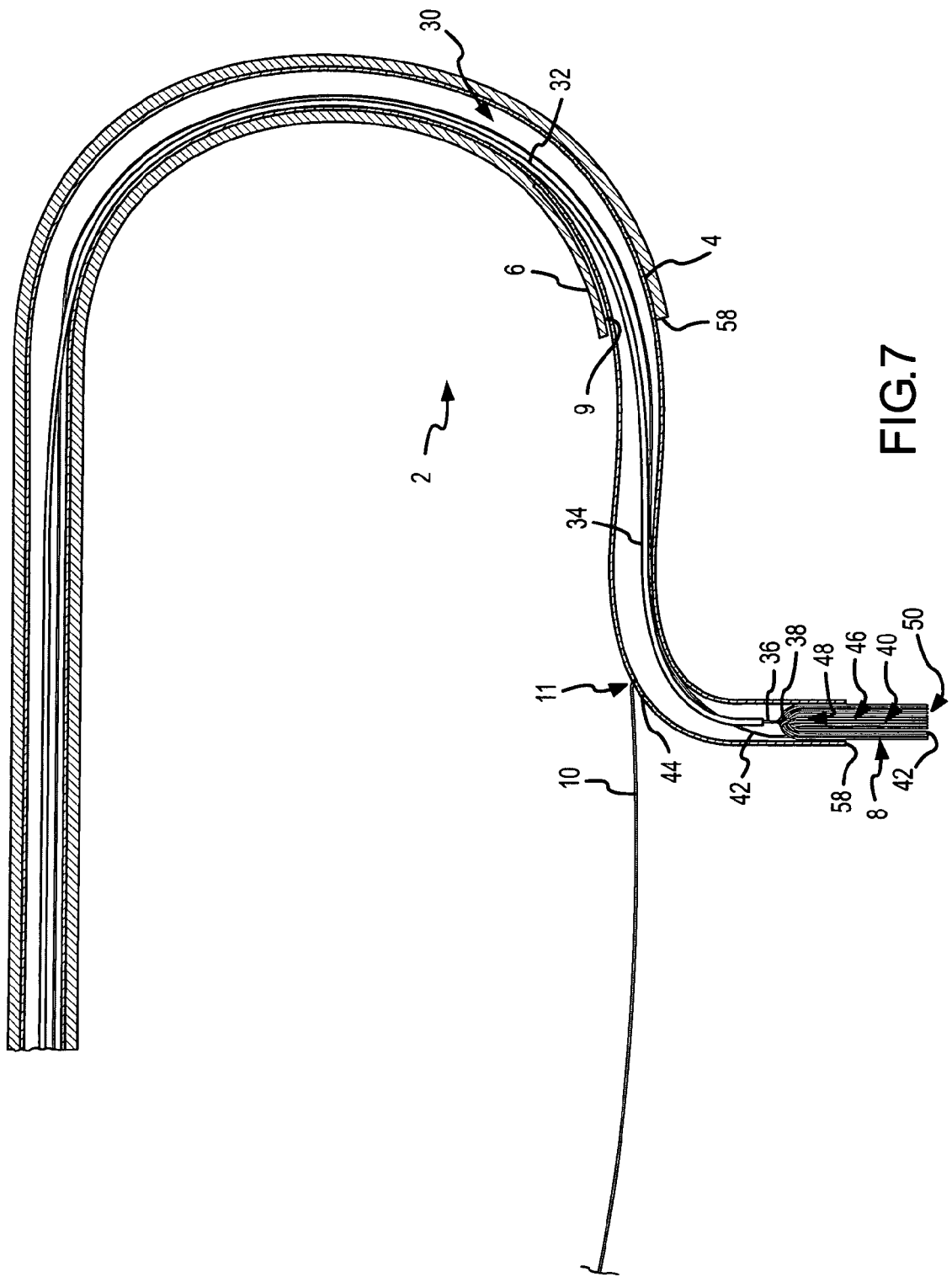

CATHETER ELECTRODE AND RAIL SYSTEM FOR CARDIAC ABLATION

BACKGROUND OF THE INVENTION a. Field of the Invention

The instant invention is directed toward an endocardial ablation catheter and sheath system incorporating wire rail system. The catheter may be pulled by or slide along the wire rail.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" utilizes a catheter to convey an electrical stimulus to a selected location within the human body to create tissue necrosis. Another procedure often referred to as "mapping" utilizes a catheter with sensing electrodes to monitor various forms of electrical activity in the human body.

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Sometimes abnormal rhythms occur in the atrium which are referred to as atrial arrhythmia. Three of the most common arrhythmia are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions which compromises cardiac hemodynamics resulting in varying levels of congestive heart failure; and (3) stasis of blood flow, which increases the vulnerability to thromboembolism. It is sometimes difficult to isolate a specific pathological cause for the arrhythmia although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate arrhythmia.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardias and atrial flutter may be lessened or eliminated. "Sufficiently deep" lesions means transmural lesions in some cardiac applications.

Ablation catheters are not presently designed to be translated within the atria while ablating to form linear lesions. Current techniques for creating continuous linear lesions in endocardial applications include, for example, dragging a conventional catheter on the tissue, using an array electrode, or using pre-formed curved electrodes. Curved electrodes have also been formed by guiding a catheter with an array electrode over a wire rail The wire rail is formed as a loop, thus guiding the distal end of the catheter into a loop form as well. The array electrodes and curved electrodes are generally placed along the length of tissue to be treated and energized to create a lesion in the tissue contiguous with the span of electrodes along the curved or looped surface.

Alternately, some catheter designs incorporate steering mechanisms to direct the distal end of the catheter. Present steerable catheter designs generally require significant technical skill on the part of the surgeon in guiding and placing the catheter by sensitive steering mechanisms and then relocating the electrode to an adjacent tissue location in order to form a continuous lesion. Because of the technical difficulty of operating catheters with such steering mechanisms, ablation procedures can be very time consuming, sometimes taking over three hours or more. Such an extended length of time can exacerbate patient discomfort, both physically and mentally. In addition, x-ray fluoroscopy is often used throughout the procedure to locate the distal end of the catheter to ensure that it is in the proper location. Clinicians are therefore exposed to significant amounts of radiation on a regular basis because of the lengthy time required for these procedures with present technology.

A particular difficulty encountered with existing ablation catheters is assurance of adequate tissue contact. All of these devices comprise rigid electrodes that do not always conform to the tissue surface, especially when sharp gradients and undulations are present, such as at the ostium of the pulmonary vein in the left atrium and the isthmus of the right atrium between the inferior vena cava and the tricuspid valve. Consequently, continuous linear lesions are difficult to achieve. With present rigid catheters of uniform construction, it can be quite difficult to maintain sufficient contact pressure until an adequate lesion has been formed. This problem is exacerbated on contoured or trabecular surfaces.

If the contact between the electrode and the tissue cannot be properly maintained, a quality lesion is unlikely to be formed. Thus, there remains a need for an ablation instrument that addresses these issues with the existing designs and that permits the formation of uniform spot and continuous linear lesions, including transmural lesions, on smooth or contoured surfaces, and that provides an ease of use not found in previous designs.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is an ablation system that is relatively simple to operate and that provides improved linear lesions on a surface of endocardial tissue. In one embodiment, the system may be composed of a catheter, an ablation electrode, a sheath, and a wire rail. The ablation electrode is positioned at a distal end of the catheter. The sheath defines a main lumen within which the catheter is received and through which the catheter is introduced into a cardiac cavity. The wire rail is received within at least a portion of the sheath and is connected with the catheter proximal and adjacent to the ablation electrode. In one embodiment, the wire rail is fixed to a wall of the catheter. In an alternative embodiment, the catheter defines an aperture and a portion of the wire rail passes through the aperture into a catheter lumen defined by the catheter. The ablation electrode may further be a brush electrode.

The sheath may further be composed of an entry portion, an anchor portion, and a spanning portion. The spanning portion is positioned distal and adjacent to the entry portion and proximal and adjacent to the anchor portion. The entry portion may define a rail port to receive the wire rail within the sheath. The entry portion is adapted to direct the sheath into the cardiac cavity. The spanning portion maintains a separation distance between the anchor portion and the entry portion. The anchor portion is curved to orient a distal tip of the anchor portion toward the rail port.

In another embodiment of the invention, the ablation system is composed of a catheter, a brush electrode, a sheath, and a wire rail. The brush electrode is positioned at a distal end of the catheter. The sheath defines a main lumen, a rail port, and a rail lumen. The rail port is proximal to a distal end of the sheath. The sheath is adapted to receive the catheter within the main lumen and introduce the catheter into a cardiac cavity. The wire rail is received within the rail lumen and extends from a proximal end of the sheath at a first end of the wire rail. The wire rail emerges from the rail port and is fixed at a second end of the wire rail to the catheter proximal and adjacent to the brush electrode.

In a further embodiment of the invention, the ablation system may be composed of a catheter, a brush electrode, a sheath, and a wire rail. The catheter defines a catheter lumen and an aperture in the wall of the catheter proximal and adjacent to a distal end of the catheter. The brush electrode is positioned at the distal end of the catheter. The sheath defines a main lumen, a rail port, and a rail lumen. The sheath is adapted to receive the catheter within the main lumen and introduce the catheter into a cardiac cavity. The rail port is proximal to a distal end of the sheath. The wire rail received within the rail lumen, extends from a proximal end of the sheath at a first end of the wire rail, and emerges from the rail port. The wire rail then passes through the aperture in the wall of the catheter, and extends from the aperture proximally through the catheter lumen wherein a second end of the wire rail is positioned adjacent the proximal end of the sheath.

The present invention is also embodied in a method of forming a linear lesion along the isthmus between the tricuspid valve and the inferior vena cava within the right atrium. The method involves introducing a sheath through the inferior vena cava into the right atrium. A first portion of the sheath is then curved to direct a second portion of the sheath and a third portion of the sheath toward the tricuspid valve. The second portion is positioned between the first portion and the third portion. The third portion of the sheath is also curved such that a distal tip of the third portion is directed toward the inferior vena cava. The third portion of the sheath is supported on a surface of the right atrium adjacent the tricuspid valve. A catheter is housed within a lumen defined by the sheath, wherein the catheter connects with a wire rail extending distally from the catheter, emerges from the lumen at the distal tip of the sheath, and reenters the sheath through a first port in the sheath proximal to the distal tip of the sheath. The catheter is deployed from the distal tip of the sheath. The distal end of the catheter is oriented toward the isthmus. An ablation electrode positioned on the distal end of the catheter is placed against the tissue of the isthmus. The ablation electrode is energized to apply energy to the tissue at a first location along the isthmus to treat the tissue. The catheter is advanced in the direction of the wire rail toward the first port in the sheath. The ablation electrode is again energized to apply energy to the tissue at a second location along the isthmus to treat the tissue. In one embodiment, the wire rail is fixed to the catheter proximal to the ablation electrode and the catheter is advanced by pulling the wire rail through the port in the sheath. In an alternate embodiment, the wire rail passes through a second port in the catheter proximal to the ablation electrode and the catheter is advanced by pushing the catheter along the wire rail toward the first port in the sheath.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 3 is an isometric view of an ablation catheter and sheath incorporating a rail system according to a second embodiment of the present invention.

FIG. 4 is an enlarged isometric view of the area of the ablation catheter as indicated in FIG. 3 detailing the interface between the wire rail and the catheter.

FIG. 5 is an alternate isometric view of a portion of the sheath of FIG. 4 detailing the interface between the wire rail and the sheath.

FIG. 7 is a cross-section view of the catheter and sheath of FIG. 1 with the catheter deployed from within the sheath.

FIGS. 12-14 are isometric schematics depicting a method of creating a linear lesion in the right atrium using the ablation catheter, sheath, and rail system of FIG. 1.

DETAILED DESCRIPTION OF THE INVENTION

Several embodiments of an endocardial ablation system, including an ablation catheter, an introducer sheath, an ablation electrode, and a wire rail, according to the present invention are depicted in the figures. As described further below, the endocardial ablation system of the present invention provides a number of advantages, including, for example, mitigating electrode-tissue contact problems. The rail system combined with the ablation catheter facilitates enhanced tissue contact in difficult environments (e.g., during ablation of a contoured or trabecular surface within a cardiac cavity) by promoting consistent linear contact of the ablation electrode with the endocardial tissue surface. The preferred brush electrode further enhances tissue contact by conforming to the contours of trabecular surfaces. This is particularly useful for treatment of atrial flutter where it is desirable to create a linear lesion along the trabecular slope of the isthmus between the ostium of the inferior vena cava and the tricuspid valve in the right atrium.

Figure 1:
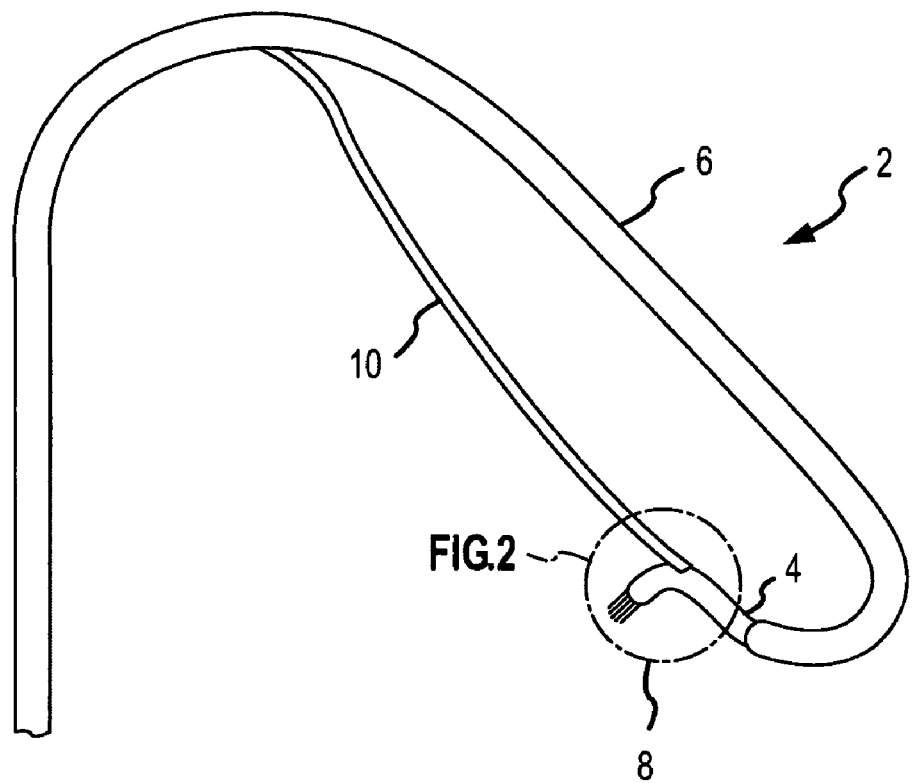
FIG. 1 is an isometric view of an ablation catheter and sheath incorporating a rail system according to a first embodiment of the present invention.

FIG. 1 is an isometric view of one embodiment of an endocardial ablation system 2 of the present invention including a catheter 4 shown emerging from a sheath 6. An ablation electrode 8 is attached to the distal end of the catheter 4. (As used herein, "proximal" refers to a direction away from the body of a patient and toward the clinician. In contrast, "distal" as used herein refers to a direction toward the body of a patient and away from the clinician.) A wire rail 10 emerges from a port 12 in the sheath 6 at a point spaced several centimeters apart from the distal tip 58 (see FIG. 6) of the sheath 6, as shown to good advantage in FIG. 5. A first end 11 of the wire rail 10 is connected with the catheter wall 44 (see FIGS. 6 and 7) adjacent to the ablation electrode 8. The opposite end (not shown) of the wire rail 10 extends to the proximal end of the sheath 6. The wire rail 10 may be housed within a rail lumen 13 (see FIG. 8) within the sheath 6 between the sheath port 12 and the proximal end of the wire rail 10. Alternately, the wire rail 10 may simply extend through the sheath port 12 into a main lumen 7 defined by the sheath 6 and travel through the main lumen to the proximal end of the sheath 6 (not shown). The catheter 4 is designed for insertion within the main lumen 7 defined by the sheath 6. Axiomatically, the diameter of the main sheath lumen 7 is sized to accommodate the outer diameter of the catheter 4.

Figure 2:
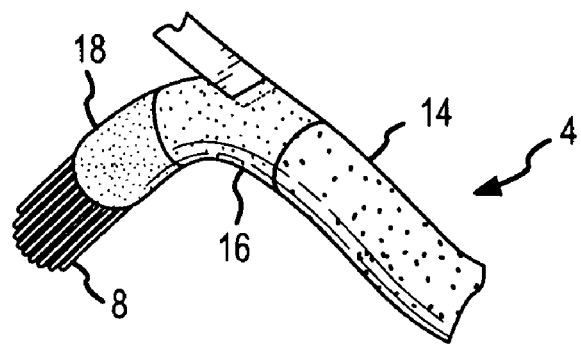
FIG. 2 is an enlarged isometric view of the area of the ablation catheter as indicated in FIG. 1 detailing several component sections of the catheter and the interface between the wire rail and the catheter.
Figure 6:
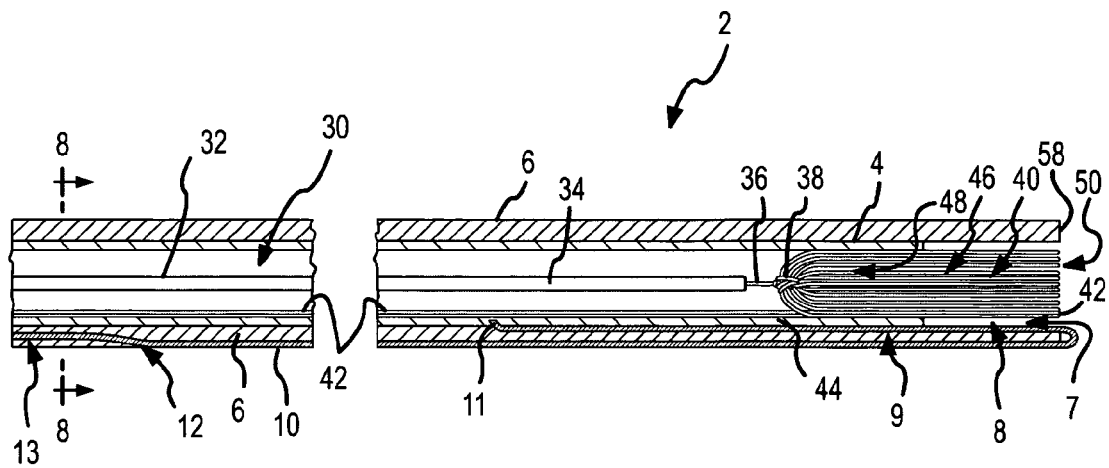
FIG. 6 is a cross-section view of the catheter and sheath of FIG. 1 with the catheter predominantly housed within the sheath.

The wire rail 10 may be a flat titanium wire as depicted in FIGS. 1 and 2. The wire rail 10 is used to pull the catheter 4 out of the sheath 6 and along the tissue to be ablated. The flat profile of the wire rail 10 provides several advantages. First, the flat cross-section opposes torsional forces that might act on the wire rail 10 to rotate it about a longitudinal axis. Such rotation may be unwanted as it could undesirably influence the orientation of the ablation electrode 8 and negatively impact the interface between the ablation electrode 8 and the tissue. Second, the flat cross-section of the wire rail 10 results in a low profile attachment of the first end 11 of the wire rail 10 with the catheter wall 44 as show in FIG. 2. Third, as shown in FIG. 6, the flat cross-section of the wire rail 10 allows the wire rail 10 to easily slide within the sheath 6, between the sheath 6 and the catheter 4, for example, when the wire rail extends within the main lumen 7 of the sheath 6 proximal to the sheath port 12 rather than in a separate lumen or when the distal end of the catheter 4 is withdrawn within the sheath 6. Because the first end 11 of the wire rail 10 is embedded in the catheter wall 44 proximal to the ablation electrode 8, when the catheter 4 is fully withdrawn within the sheath 6, a portion of the wire rail 10 will wrap around the distal tip 58 of the sheath 6 and will be pulled within the lumen 7 of the sheath 6. In one embodiment, the wall of the sheath 6 may be formed with a linear recess or trough 9 within which the wire rail 10 may reside. The trough 7 can alleviate any binding between the catheter 4 and sheath 6 that otherwise might occur when the wire rail 10 is drawn into the distal tip 58 of the sheath 6.

FIGS. 3 and 4 depict an alternative embodiment of an endocardial ablation system 2' according to the present invention. In this embodiment, the wire rail 10' is a single long loop beginning and ending at the proximal end of the sheath 6 and catheter 4'. The wire rail 10' exits the sheath 6 as in the first embodiment through the sheath port 12 in the wall of the sheath 6, as shown to good advantage in FIG. 5. The sheath port 12 may be in the entry portion 22 of the sheath 6 as described further below. Instead of an end of the wire rail being attached to the catheter as in FIG. 1, the wire rail 10' slides through a port 28 in the catheter 4'. The catheter port 28 may be in a suspension section 16 of the catheter as further described below. The wire rail 10' may then extend proximally within the catheter lumen 30 (see FIGS. 9 and 10) until it terminates at a handle (not shown) operated by the clinician. The catheter 4' freely slides along a length of the wire rail 10' that emerges from the sheath port 12 as the catheter 4' is deployed from and retracted into the sheath 6. The wire rail 10' maintains a generally constant length external to the sheath 6 once the sheath 6 is appropriately placed in the cardiac cavity. However, portions of the wire rail 10' external to the sheath 6 are enclosed within the catheter lumen 30 as the catheter 4' is moved distally and the wire rail 10' enters the catheter port 28. As in the first embodiment, the wall of the sheath 6 may be formed with a linear recess or trough 9 within which the wire rail 10' may reside as the catheter 4' and wire rail 10' are drawn within the sheath 6.

As shown in FIG. 2, the catheter 4 may be a component-built catheter, in this embodiment divided into three sections, a proximal section 14, a suspension section 16, and a distal section 18. The suspension section 16 is located between the proximal section 14 and the distal section 18. In one embodiment, both the proximal section 14 and the distal section 18 may be of a more rigid construction than the suspension section 16, which is comparatively pliant. While more rigid than the suspension section 16, the proximal section 16 and the distal section 18 may each have different levels of stiffness or rigidity. In other embodiments it may be desirable to include additional component sections of varying degrees of rigidity depending upon the need of the procedure to be performed. For example, the distal section 18 might be formed of a soft or pliable material to minimize abrasion of the endocardial tissue. In addition, the proximal section 14 extending proximally toward the clinician may be more rigid, allowing the catheter 4 to more easily translate the manipulations imparted by the clinician.

Figure 17:
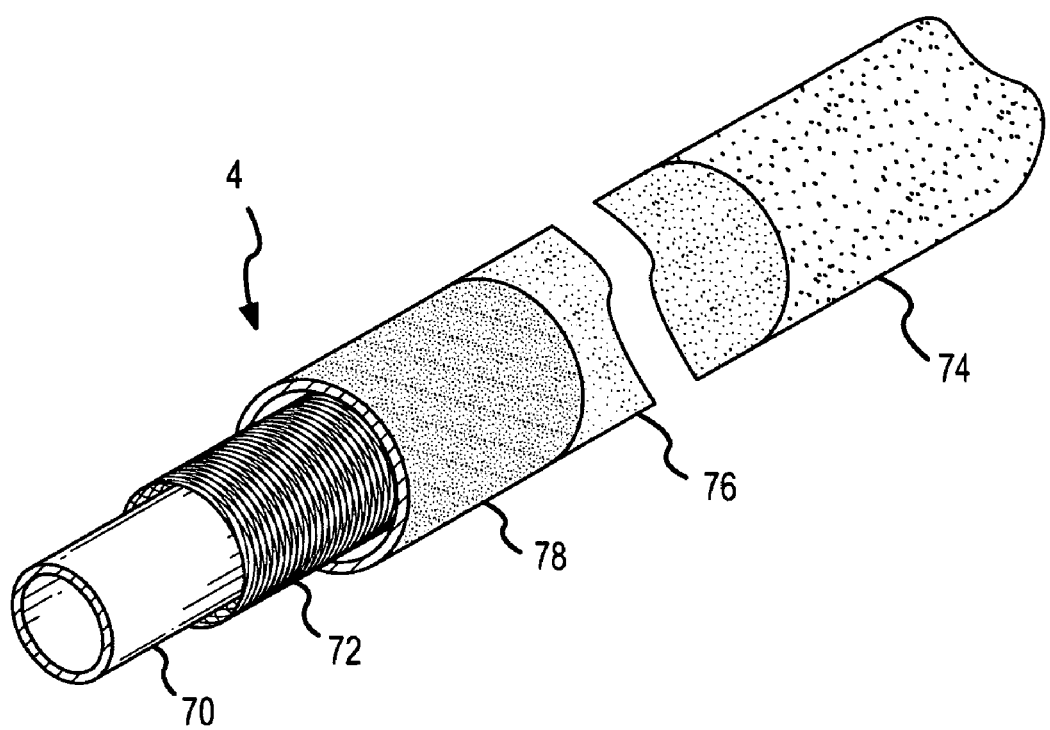
FIG. 17 is an isometric schematic of the various component materials forming the catheter of the present invention.
Figure 18:
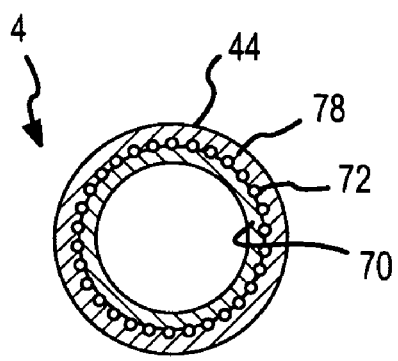
FIG. 18 is a cross-section of a catheter formed of the material components of FIG. 17.

FIGS. 17 and 18 depict one exemplary embodiment for forming such a component catheter 4 from sections of different materials as indicated in FIG. 2. The catheter wall 44 may be formed of several layers of materials to ultimately create a composite structure. In the embodiment of FIGS. 17 and 18 the catheter wall 44 is composed of an inner tube 70 of plastic, which is initially surrounded by a cylindrical braid 72 of metal fibers, for example, stainless steel fibers. The metallic braid 72 is included in the catheter wall 44 to add stability to the catheter 4 and also to resist radial forces that might crush the catheter 4. The metallic braid 72 also provides a framework to translate torsional forces imparted by the clinician on the proximal section 14 to the distal end to rotate the catheter 4 for appropriate orientation of the ablation electrode 8. The choice of a flat, angled braid pattern for the metallic braid 72 as depicted adds hoop strength to the catheter 4 without impacting the flexibility of the catheter 4. Based upon the exemplary configuration of FIG. 2, three collinear sections of equal diameter plastic tubing abutted together surround the metallic braid 72. A first tube 74 is composed of a first plastic material, a second tube 76 is composed of a second plastic material, and a third tube 78 is composed of a third plastic material.

The component plastic sections of the catheter wall 44 may be composed, for example, of Pebax® resins (AUTO-FINA Chemicals, Inc., Philadelphia, Pa.), or other polyether-block co-polyamide polymers, wherein different formulas are used to create the desired material stiffness within each section of the catheter 44. These sections of different material enable the catheter 4 to have, for example, different mechanical properties (e.g., flexibility) at different locations along the catheter shaft. For example, the proximal section 14 of the catheter wall 44 may be formed by the first tube 74 having a relatively stiffer material formulation than the suspension section 16 to aid in maintaining a desired orientation of the ablation electrode 8. The suspension section 16 may be formed by the second tube 76 having a relatively more pliable material formulation than the first tube 74 of the proximal section 14 to provide a level of suspension to the distal tip 18 as further described below. The distal section 18 may be formed by the third tube 78 also having a relatively more rigid material formulation than the suspension section 16 to provide appropriate support to the ablation electrode 8. The inner tube 70 is generally chosen to have a relatively pliant material formulation. In an exemplary embodiment, the first tube 74 may have a hardness of 72 Shore A, the second tube 76 may have a hardness of 55 Shore A, the third tube 78 may have a hardness of 65 Shore A, and the inner tube 70 may have a hardness of 40 Shore A. The distal section 18 may further be composed of a radiopaque marker to allow a clinician to visualize the position of the tip of the catheter 4 within the heart.

Once the appropriate material qualities of the plastic for each of the inner, first, second, and third tubes 70, 74, 76, 78 are chosen, the catheter wall 44 can be fabricated. As previously described, the inner tube 70 is first surrounded by the metallic braid 72. The first, second, and third tubes 74, 76, 78 are then placed around the metallic braid 72 and are abutted together, end-to-end. The first, second, and third tubes 74, 76, 78 may then be covered by a shrink wrap tube (not shown), if desired, to maintain the close abutment between the adjacent ends of the first, second, and third tubes 74, 76, 78. The layered structure of the inner tube 70, the metallic braid 72, the first, second, and third tubes 74, 76, 78, and the shrink wrap is then heated to a temperature at which the plastic materials composing each of the inner, first, second, and third tubes 70, 74, 76, 78 begin to melt. The plastic of the inner tube 70 flows through the interstices of the metallic braid 72 from the inside. Similarly, the plastic of the first, second, and third tubes 74, 76, 78 flows through the interstices of the metallic braid 72 from the outside. In this manner, the inner tube 70 is welded to the first, second, and third tubes 74, 76, 78 and the metallic braid 72 is encapsulated between them to form the catheter wall 44 as shown in FIG. 18. Similarly, the adjacent ends of the first tube 74 and second tube 76 are welded together and the adjacent ends of the second tube 76 and the third tube 78 are welded together. If the shrink wrap tube is used, it encapsulates the entire catheter wall 44 of the component catheter 4. Although the catheter wall 44 depicted in the figures (and as shown in cross-section in FIG. 18) has a circular cross section, the cross-section of the catheter wall 44 may be other than circular.

Figure 9:
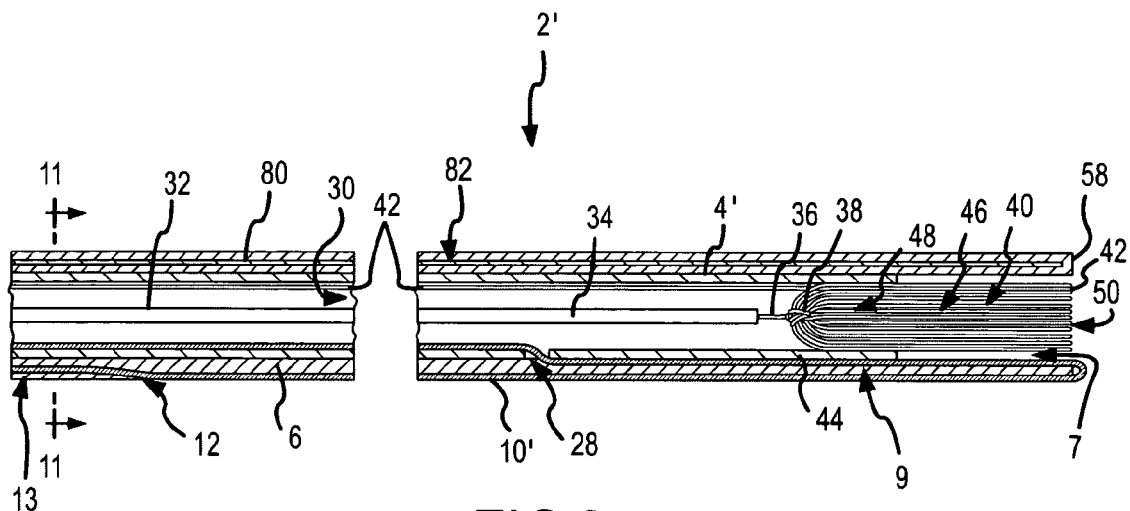
FIG. 9 is a cross-section view of the catheter and sheath of FIG. 3 with the catheter predominantly housed within the sheath.

If desirable, certain of the component sections may be formed with curved shapes to assist the placement of the catheter 4 based upon the anatomy of the heart. Such curvature can be imparted to the catheter 4, for example, by placing a mandrel of a desired form in the catheter 4 and thermally setting the desired curvature to the catheter wall 44. For example, as shown in FIG. 2, the curved suspension section 16 is curved to orient the distal section 18 of the catheter 4 toward the tissue surface to be ablated (see FIGS. 12-16). The arc or radius of curvature of a particular section may be selected to allow the catheter 4 to appropriately "fit" in various sizes of heart cavities, to position the catheter 4 with respect to a particular tissue location for ablation application, or to orient the attached ablation electrode 8 at a particular angle or direction. As indicated in FIGS. 6 and 9, each of the sections of the catheter 4 is pliant compared to the sheath 6 and, when introduced into the sheath 6, each of the sections of the catheter 4 is constrained by the sheath 6 and conforms to the orientation of the sheath 6. However, once released from the sheath 6, the catheter 4 will assume the preformed shape imparted to it during manufacture, as shown in FIGS. 7 and 10.

The introducer sheath 6 may similarly be composed of several component sections of different materials as indicated in FIG. 3. A proximal portion 20 of the sheath 6 is connected with an entry portion 22, which is connected with a spanning portion 24, which is in turn connected with an anchor portion 26, which forms the distal end of the sheath 6. Similar to the catheter 4, each of the proximal portion 20, the entry portion 22, the spanning portion 24, and the anchor portion 26 may be composed, for example, of Pebax® resins. The proximal portion 20, the entry portion 22, the spanning portion 24, and the anchor portion 26 may be of the same or different material formulations with similar or different hardness measurements depending upon the needs of the particular procedure to be performed. In this application, the hardness of the plastic formulations for the component section of the sheath 6 may be greater than that of the catheter 4 in order to guide the catheter 4 within the main lumen of the sheath 6.

Each of the entry portion 22, the spanning portion 24, and the anchor portion 26 may be sized appropriately to fit within the cardiac cavity to be ablated. Different standard sizes for the component sections of the sheath 6 may be available for use depending upon the size of a particular patient's cardiac cavity. Further, as with the catheter 4, the entry portion 24 may be curved to direct the sheath 6 and ultimately the catheter 4 into the cardiac cavity. The anchor portion 26 may also be curved to appropriately orient the distal end of the catheter 4 to the area of tissue to be treated. However, because the sheath 6 is used to negotiate the vasculature, unlike with the catheter 4, it may be inappropriate to fix portions of the sheath 6 into preformed shapes. A sheath 6 with preformed curves might be unable to travel through the vasculature or, more problematically, introducing a preformed shape into the vasculature may injure the vasculature, for example, tearing a vessel and causing bleeding.

Figure 11:
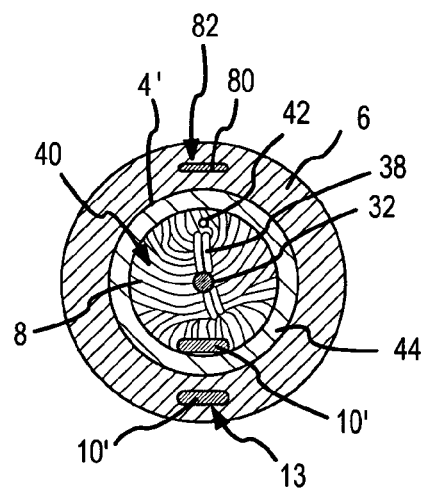
FIG. 11 is a cross-section view, taken along line 8-8 of FIG. 6, of the catheter and ablation electrode within the sheath.
Figure 10:
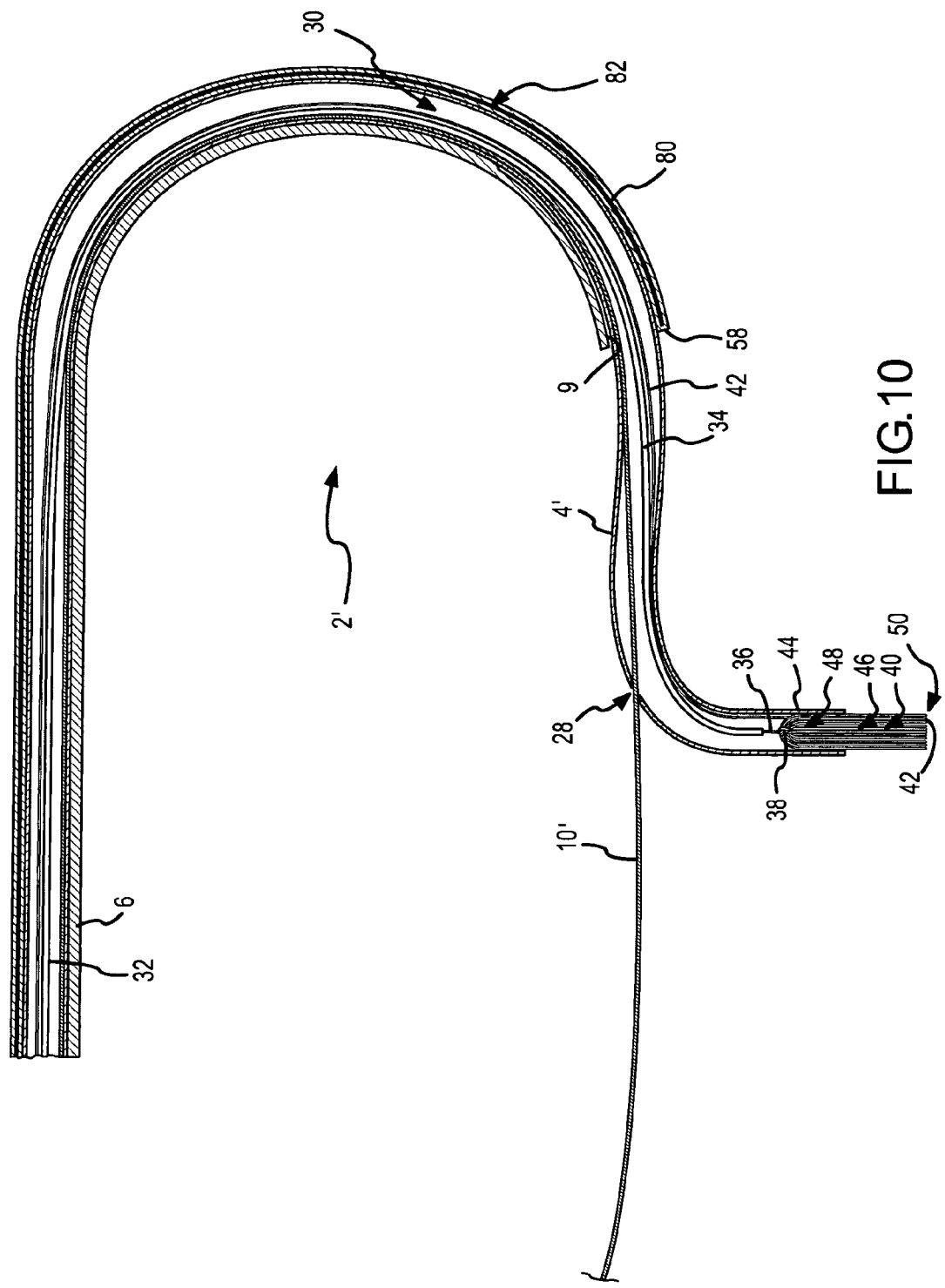
FIG. 10 is a cross-section view of the catheter and sheath of FIG. 3 with the catheter deployed from within the sheath.

In one embodiment, the entry portion 22, the spanning portion 24, and the anchor portion 26 may be formed by the inclusion of a shape-memory metal wire 80 within a wire lumen 82 defined within the wall of the sheath 6 as depicted in FIGS. 9-11. The shape-memory wire 80 is flexible while the clinician negotiates the sheath 8 through the vasculature to reach the heart and enter an atrial chamber. Once the distal end of the sheath 6 reaches the desired cardiac cavity, the shape-memory wire 80 can be caused to assume a pre-formed shape to accurately orient the sheath 6 within the cardiac cavity for the procedure to be performed. The shape-memory wire 80 also exhibits increased tensile strength once the transformation of to the pre-formed shape is completed. The shape-memory wire 80 may be used to curve the sheath 6 into the right atrium once it emerges from the inferior vena cava (see, e.g., FIG. 12) thereby forming the entry portion 22. Similarly, the shape-memory wire 80 may be used to curve the distal end of the sheath 6, thereby forming the anchor portion 26. In the embodiment shown in FIG. 12, the anchor portion 26 orients the catheter 4 toward the inferior vena cava. The anchor portion 24 may be pressed or anchored against tissue in a cavity of the heart, for example, an atrial wall 56 as shown in FIGS. 12-16, to help stabilize the endocardial ablation system 2 while the heart is beating. Further, the shape-memory wire 80 may be used to keep the spanning portion 24 straight to maintain the separation distance between the entry portion 22 and the anchor portion 26 for appropriate positioning of the catheter 4 and ablation electrode 8 within the cardiac cavity.

For example, a shape-memory wire 80 of NiTinol, a nickel-titanium (NiTi) alloy with shape-memory properties may be included within the sheath 6. Shape-memory metals, such as NiTinol, are materials that have been plastically deformed to a desired shape before use. Then upon heat application, either from the body as the sheath 6 is inserted into the vasculature or from external sources, the shape-memory material is caused to assume its original shape before being plastically deformed. NiTinol and other shape-memory alloys are able to undergo a "martenistic" phase transformation that enables them to change from a "temporary" shape to a "parent" shape at temperatures above a transition temperature. Below the transition temperature, the alloy can be bent into various shapes. Holding a sample in position in a particular parent shape while heating it to a high temperature programs the alloy to remember the parent shape. Upon cooling, the alloy adopts its temporary shape, but when heated again above the transition temperature the alloy automatically reverts to its parent shape. Alternately, or in addition, shape-memory materials may also be super elastic—able to sustain a large deformation at a constant temperature—and when the deforming force is released they return to their original undeformed shape.

Common formulas of NiTinol have transformation temperatures ranging between −100 and +110° C., have great shape-memory strain, are thermally stable, and have excellent corrosion resistance, which make NiTinol exemplary for use in medical devices for insertion into a patient. For example, the entry, spanning, and anchor portions 22, 24, 26 may be designed using NiTinol with a transition temperature around or below room temperature. Before use the sheath 6 is stored in a low-temperature state. By flushing the sheath 6 with chilled saline solution, the NiTinol entry, spanning, and anchor portions 22, 24, 26 can be kept in the deformed state while positioning the sheath 6 at the desired site. When appropriately positioned, the flow of chilled saline solution can be stopped and the sheath 6 warmed by body heat, or warm saline can be substituted, to allow the NiTinol to recover its "preprogrammed" shape.

Figure 15:
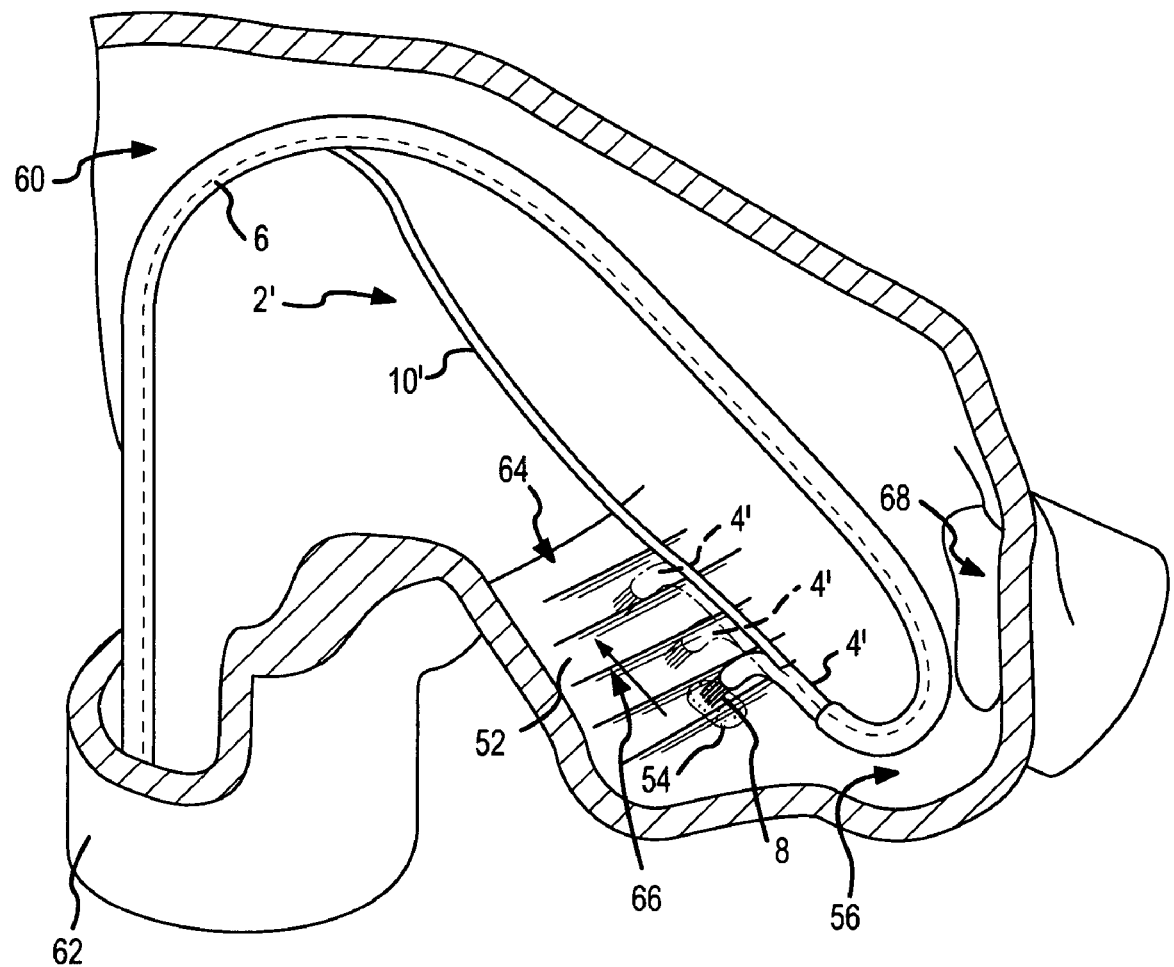
FIG. 15 is an isometric schematic depicting a method of creating a linear lesion in the right atrium using the ablation catheter, sheath, and rail system of FIG. 3 depicting a method of creating a linear lesion in the right atrium.
Figure 16:
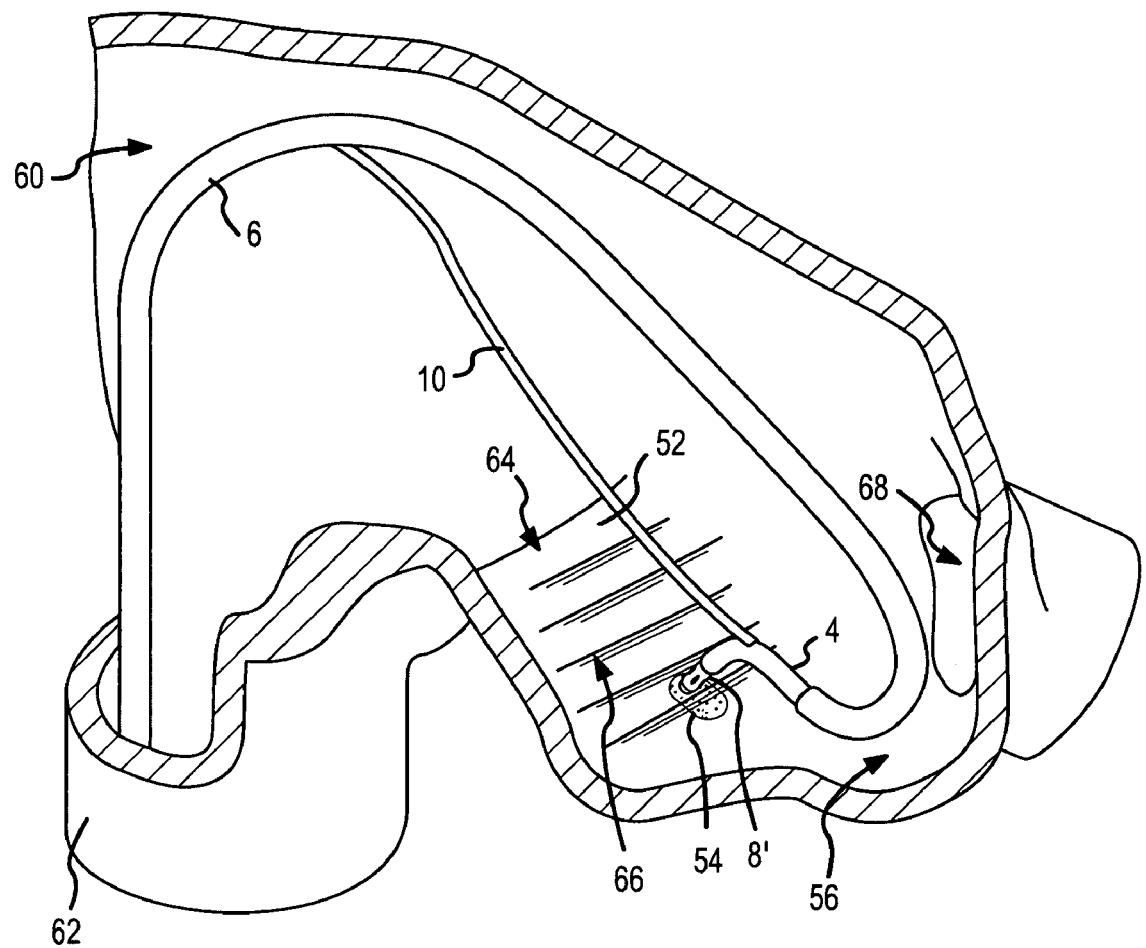
FIG. 16 is an isometric schematic of an alternate embodiment of the ablation catheter of the present invention with a ball electrode depicted in situ in the right atrium.

In the particular embodiment of FIGS. 1-4 and 6-11, a brush electrode 8 is depicted as the ablation electrode 8. A continuous linear lesion 54 (as shown in FIGS. 12-15) is able to be formed because of the superior ability of the filaments 40 of the brush electrode 8 to maintain contact with the tissue 52 and to transfer ablative energy to the tissue 52. In an alternative embodiment, for example, as shown in FIG. 16, the catheter 4 may incorporate a ball electrode 8' as the ablation electrode. Although not as capable of conforming to trabecular surfaces as the brush electrode 8, the ball electrode 8' may be desired for use in certain circumstances for creating spot ablations. Other electrode tips known in the industry may alternately be used if so desired.

The novel brush electrode 8 of the type depicted in FIGS. 1-4 and 6-11 was originally disclosed in U.S. patent application Ser. No. 10/808,919 filed 24 Mar. 2004, entitled *Brush Electrode and Method for Ablation*, which is hereby incorporated by reference in its entirety as though fully set forth herein. As shown in greater detail in FIGS. 6-11, the brush electrode 8 may be composed of a plurality of filaments 40, either conductive or nonconductive, arranged in a bundle and protruding from the distal section 18 of the catheter 4. Such a flexible brush electrode 8 provides enhanced tissue contact, particularly for use on contoured or trabecular surfaces.

The filaments 40 may be constructed from a variety of different materials, including nonconductive materials, semi-conductive materials, and conductive materials. For example, the filaments 40 may be formed from metal fibers, metal plated fibers, carbon compound fibers, and other materials. Very thin, carbon fibers may be used. Relatively thicker but less conductive Thunderon® acrylic fibers (Nihon Sanmo Dyeing Company Ltd., Kyoto, Japan) may also be used for the brush electrode filaments 40. Nylon fibers coated with conductive material may also be used. Filaments 40 constructed from metal plated fibers, like coated nylon fibers, may comprise flattened areas around their outer surfaces, resulting in the filaments 40 having noncircular cross-sectional shapes. The brush filaments 40 may be insulated from each other, or they may be in electrical contact with each other. Conductive or nonconductive fluids may flow interstitially between and among the filaments 40 themselves or along the outer surface of the filaments 40.

An embedded portion 48 of the filaments 40 forming the brush electrode 8 may be contained within the catheter lumen 30 of the distal section 18 of the catheter 4 while an exposed portion 46 may extend distally from the distal section 18. The exposed portion 46 of the brush electrode 8 may project a few millimeters from the distal section 18 of the catheter 4. The distance that the exposed portion 46 of the brush electrode 8 extends from the distal section 18 of the catheter 4 varies depending upon a number of factors including the composition of the filaments 40 comprising the brush electrode 8 and the particular area to be treated with the brush electrode 8. The distal section 18 of the catheter 4 may itself be conductive or nonconductive.

FIG. 6 is a cross-section view of the ablation system 2 of FIG. 1 with the catheter 4 and the brush electrode 8 generally contained within the main lumen of the sheath 6. FIG. 7 is similarly a cross-section view of the ablation system 2 of FIG. 1, in this instance with the catheter 4 and the brush electrode 8 unfurling from the sheath 6. As depicted in FIGS. 6 and 7, the catheter houses a conductor 32 having an insulated portion 34 and an uninsulated portion 36 that carries ablative energy (e.g., radio frequency current) from an energy source in a controller (not shown) to the brush electrode 8. The conductor 32 extends within the catheter lumen 30 along a longitudinal axis of the catheter 4. The conductor 32 may comprise, for example, insulated copper wire with an uninsulated portion 36 in electrical contact with the brush electrode 8.

Figure 8:
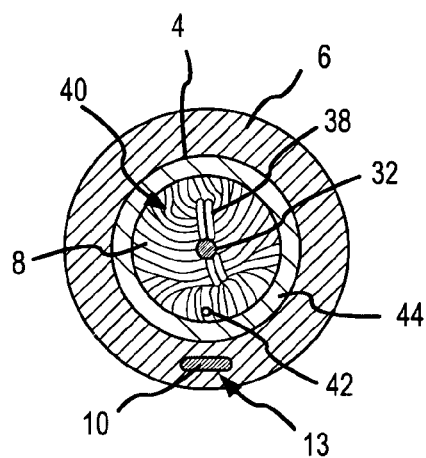
FIG. 8 is a cross-section view, taken along line 8-8 of FIG. 6, of the catheter and ablation electrode within the sheath.

In this embodiment, the uninsulated portion 36 of the conductor 32 is formed or tied in a loop or noose 38 around the embedded portion 48 of the filaments 40 of the brush electrode 8 as shown in FIGS. 6-8. At the loop or noose 38, ablative energy is transferred from the conductor 32 to the conductive filaments 40 of the brush electrode 8. In this embodiment, the uninsulated portion 36 of the conductor 32 is connected to the embedded portion 48 of the brush electrode 8 so that the connection between the conductor 32 and the brush electrode 8 is protected within the catheter wall 44. A lead 42 may extend substantially parallel to the conductor 32. A distal end of the lead 42 is embedded with the filaments 40 comprising the brush electrode 8. The lead 42, when present, may be operatively connected to a sensor embedded in the brush electrode 8 (e.g., a thermal sensor, an ultrasound sensor, or a pressure sensor).

As shown in FIGS. 6-11, the brush electrode 8 may have a relatively flat working surface 50 at the distal end of the brush electrode 8. In other words, in this depicted embodiment, all of the filaments 40 comprising the brush electrode 8 extend approximately the same distance from the distal section 18 of the catheter 4. Thus, the brush tip provides a relatively flat working surface 50 comprising the longitudinal ends of the filaments 40. The catheter wall 44 of the distal section 18 of the catheter 4 provides mechanical support for the filaments 40 and may also provide electrical shielding.

The filaments 40 may alternatively be trimmed to provide a variety of configurations and shapes for the working surface 30 of the brush electrode 8, which may provide advantages for special applications of the brush electrode 8. For example, a blade-shape may be formed by creating an edge of longer filaments of the brush electrode 8 resulting in a line of contact with the tissue. Alternatively, the brush electrode 8 may have a wedge-shaped working surface 50 to facilitate angular placement and increase the area of the working surface 50. This configuration may be advantageous for point applications of ablative energy. As another example, the working surface 50 of the brush electrode 8 may have a concave portion or channel, which may be beneficial for wrap-around applications and provide advantages when ablating curved surfaces like the outer surface of a blood vessel. Alternatively, the working surface 50 of the brush electrode 8 may have a convex, trough-shaped tip, which may be beneficial, for example, when reaching into troughs or depressions on a contoured surface. The working surface 50 of the brush electrode 8 may also be domed, hemispherical, a frustum, or conical, coming nearly to a point at the most distal end of the brush electrode 8, with its longest filaments 40 proximal to the longitudinal axis of the catheter 4. The brush electrode 8 is depicted in many of the drawings with a circular cross section, but it may have different cross-sectional configurations.

In one embodiment, as shown in FIGS. 6, 7, 9, and 10, conductive or nonconductive fluid may flow through the catheter lumen 30 from a fluid source (e.g., a pump and reservoir in a controller) to the brush electrode 8. When the fluid flows through the brush electrode 8, it creates a wet-brush electrode in which impinging jets of fluid traveling interstitially impact the tissue 52 at an interface between the tissue 52 and the brush electrode 8 to help control temperature changes at the interface. When using conductive fluid and either conductive or nonconductive filaments 40, the brush electrode 8 may act as a virtual electrode. If there is no direct contact between conductive filaments and the tissue 52, or the filaments 40 are entirely nonconductive, the conductive fluid flowing through the catheter lumen 30 makes the electrical contact at the interface between the brush electrode 8 and the tissue 52.

The brush electrode 8 according to the present invention delivers ablative energy to the tissue via the conductive filaments 40 alone, via the conductive fluid alone, or via both the conductive filaments 40 and the conductive fluid. In the latter two configurations, the brush electrode 8 is referred to as a wet-brush electrode. Since it is possible for the conductive fluid to escape from the exposed portion of the wet-brush electrode before reaching the working surface 50 at the distal tip of the wet-brush electrode, there is some ablative energy leakage to the surrounding blood. The leakage of ablative energy to the surrounding blood is in part due to direct contact between the blood and the conductive filaments and in part due to the conductive fluid escaping between the filaments 40 to the surrounding blood, particularly when substantial splaying of the filaments 40 occurs.

Figure 12:
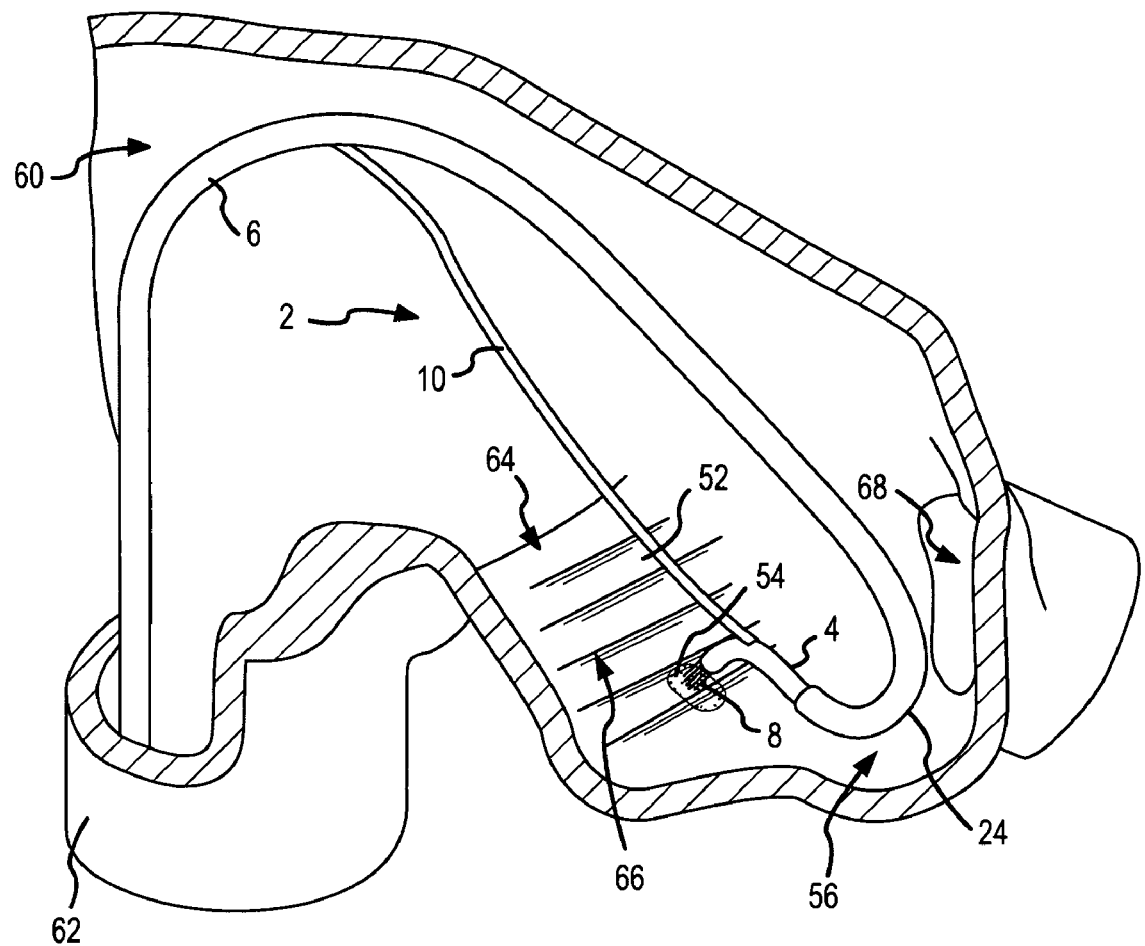
FIG. 12 is a cross-section of a catheter formed of the material components of FIG. 11.
Figure 13:
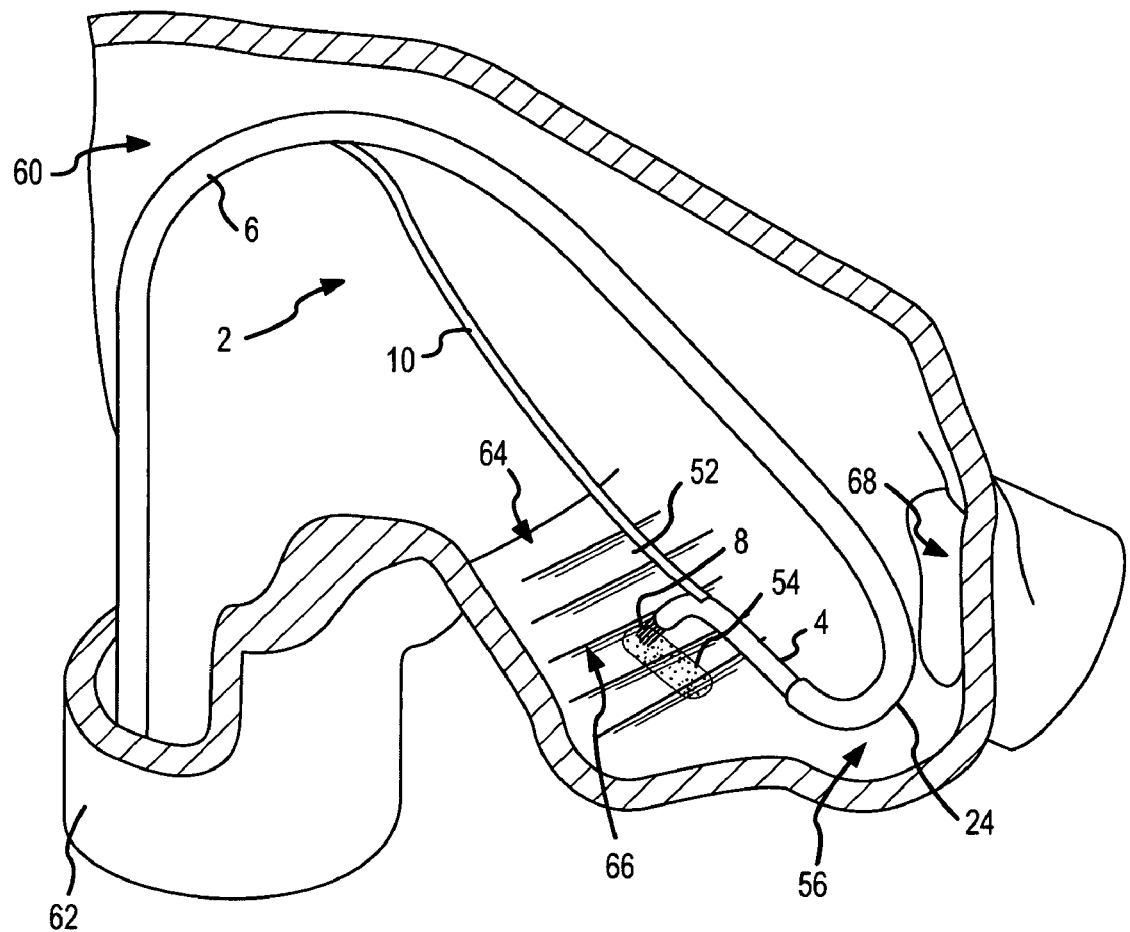
Figure 14:
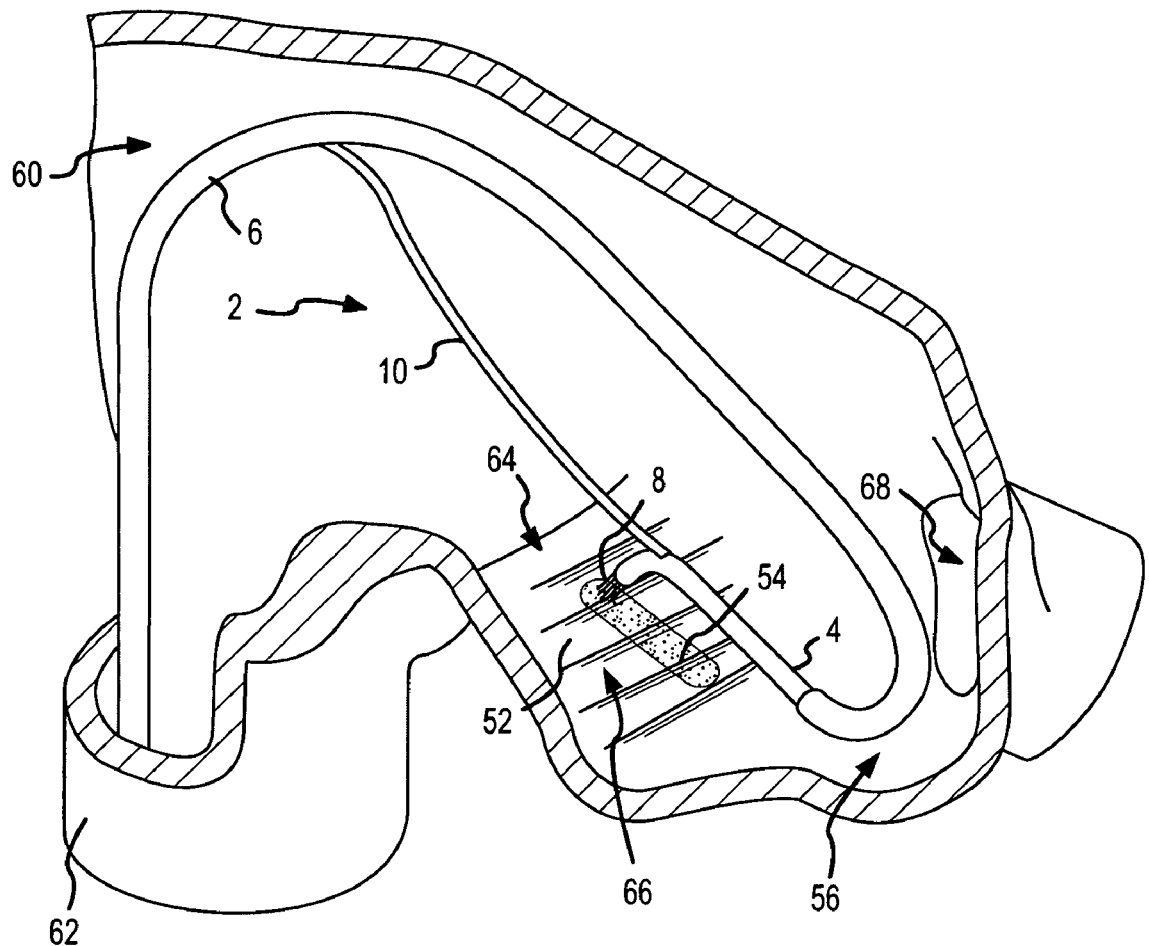

The creation of a linear lesion 54 in the tissue 52 of the isthmus 64 of the right atrium 60 using the endocardial ablation system 2 of FIG. 1 is depicted schematically in FIGS. 12-14. Similarly, the creation of a linear lesion 54 in the tissue 52 of the isthmus 64 of the right atrium 60 using the endocardial ablation system 2' of FIG. 3 is depicted schematically in FIG. 15. In these procedures, a linear series of ablation lesions is created from the annulus of the tricuspid valve 28 to the inferior vena cava 22 in the isthmus 24 of the right atrial tissue 52 bordering the Eustachian ridge. This isthmus 24 of tissue is critical to the large right atrial reentrant circuit responsible for atrial flutter. The ablation lesions 54 damage atrial tissue 52 preventing the conduction of electrical impulses through the critical isthmus 24. When the line of conduction block is complete, the atrial flutter circuit is shorted and the arrhythmia is cured.

In both the endocardial ablation system 2 of FIG. 1 and the endocardial ablation system 2' of FIG. 3, the sheath 6 is positioned as desired in the heart, for example, in the right atrium 60. As shown in FIG. 12, as the sheath 6 enters the right atrium 60 from the inferior vena cava 62, the entry portion 22 directs the sheath 6 toward the tricuspid valve 68. The spanning portion 24 traverses the cavity of the right atrium 60, generally parallel to the isthmus 64 to locate the anchor portion 26 against the atrial wall 56 adjacent the tricuspid valve 68. The anchor portion 26 of the sheath 6 forms a 180° angle to orient the distal tip 58 of the sheath 6 toward the inferior vena cava 62. The curve of the anchor member 26 is set securely against the atrial wall 56 by the length of the spanning portion 24. This placement of the sheath 6 fixes the position of the ablation system 2, 2' and minimizes movement of the ablation system 2, 2' with respect to the heart when the heart beats.

Using the ablation system 2 of FIG. 1, a linear lesion 54 is initiated by the deployment of the catheter 4 from the distal tip 58 of the sheath 6 as shown in FIG. 12. When moved distally out of the sheath lumen 7, the suspension section 16 of the catheter 4 curves to orient the distal section 18 toward the tissue 52, initially along the sloped isthmus 64 adjacent the tricuspid valve 68. The working surface 50 of the ablation electrode 8 is thereby placed generally orthogonal to and in contact with the tissue 52. The suspension section 16, being of a relatively pliable construction, bends easily to allow the distal section 18 to orient appropriately. By creating an orthogonal orientation, a greater surface area of the working surface 50 of the ablation electrode 8 is placed in contact with the tissue 52. Upon activation of a source of ablative energy connected with the ablation electrode 8, the tissue 52 is necrotized and a lesion 54 is formed.

To create a linear lesion along the isthmus 64 of the right atrium 60, the catheter 4 is manipulated to both relocate the ablation electrode 8 along trabecular surface 66 of the isthmus 2 and maintain the orientation of the distal section 18 generally orthogonal to the tissue 52. From the initial position the catheter 4 may be pulled distally from the sheath lumen 7 by the clinician pulling on the wire rail 10, as shown in FIGS. 13 and 14. In this manner, the directional section 18 of the catheter 4 to which the wire rail 10 is attached, and consequently the ablation electrode 8, is pulled along the isthmus 64. Once the catheter 4 is moved distally a small amount to reposition the ablation electrode 8, the energy source can again be activated to treat the tissue 52 and increase the size of the lesion 54.

By pulling the catheter 4 with the wire rail 10, the clinician is better able to ensure that a linear lesion 54 is formed. The sheath port 12 through which the wire rail 10 enters the sheath 6 maintains a fixed position with respect to the distal tip 58 of the sheath 6. A linear path is thus followed by the catheter 4 from the distal tip 58 of the sheath 6 toward the sheath port 12 as the wire rail 10 is pulled by the clinician. The pliability of the suspension section 16 acts as a suspension, allowing the ablation electrode 8 to easily follow the undulations of the trabecular surface 66 of the isthmus 64. The pliable filaments 40 of the brush electrode 8 also ensure good contact with the tissue 52. By maintaining a close interface between the ablation electrode 8 and the endocardial tissue 52 on the isthmus 64 along a linear path as shown in FIGS. 12-14, a continuous linear lesion 54 may be created.

In an alternate embodiment, using the ablation system 2' of FIG. 3, a linear lesion 54 is also initiated by the deployment of the catheter 4 from the distal tip 58 of the sheath 6. As shown in FIG. 15, as the catheter 4' is pushed distally by the clinician from the sheath lumen 7, the catheter 4' slides along the wire rail 10'. When moved distally out of the sheath lumen 7, the suspension section 16 of the catheter 4' again curves to orient the distal section 18 toward the tissue 52, initially along the sloped isthmus 64 adjacent the tricuspid valve 68. The working surface 50 of the ablation electrode 8 is thereby placed generally orthogonal to and in contact with the tissue 52. The suspension section 16, being of a relatively pliable construction, bends easily to allow the distal section 18 to orient appropriately. By creating an orthogonal orientation, a greater surface area of the working surface 50 of the ablation electrode 8 is placed in contact with the tissue 52. Upon activation of a source of ablative energy connected with the ablation electrode 8, the tissue 52 is necrotized and a lesion 54 is formed.

From the initial position the catheter 4' may be further pushed distally from the sheath lumen 7 by the clinician at the proximal end of the sheath 6. In this manner, the wire rail 10' slides through the catheter port 28 in the directional section 18 of the catheter 4. Consequently the ablation electrode 8, is pushed along the isthmus 64. Once the catheter 4' is moved distally a small amount to reposition the ablation electrode 8, the energy source can again be activated to treat the tissue 52 and increase the size of the lesion 54. By pushing the catheter 4 over the wire rail 10', the clinician is better able to ensure that a linear lesion 54 is formed. The sheath port 12 through which the wire rail 10 enters the sheath 6 maintains a fixed position with respect to the distal tip 58 of the sheath 6. A linear path is thus followed by the catheter 4' from the distal tip 58 of the sheath 6 toward the sheath port 12 as the catheter 4' is pushed along the wire rail 10 by the clinician. The pliability of the suspension section 16 acts as a suspension, allowing the ablation electrode 8 to easily follow the undulations of the trabecular surface 66 of the isthmus 64. By maintaining a close interface between the ablation electrode 8 and the endocardial tissue 52 on the isthmus 64 along a linear path as shown in FIG. 15, a continuous linear lesion 54 may be created.

In this manner, the endocardial ablation system 2, 2' of the present invention provides a simple mechanism to direct an ablation electrode to treat a sloped trabecular surface 26 along the isthmus 24 between the inferior vena cava 62 and the tricuspid valve 68 in the right atrium 60. The preset curves of the suspension section 16 of the catheter and the anchor portion 26 of the sheath 6 maintain the orientation of the ablation electrode 8 toward the trabecular slope 66. Further, because of the pliability of the suspension section 16, the distal section 18 may maintain an orthogonal orientation to the isthmus 64 at any point along the trabecular slop 66. This allows the ablation electrode 8 of the catheter to contact any portion of the trabecular slope 66 desired. This is achievable by merely introducing the catheter into the right atrium 60 through the sheath 6 and manipulating the catheter 4 distally by either pulling the wire rail 10, as in FIGS. 12-14, or by sliding the catheter 4' along the wire rail 10", as in FIG. 15. Thus, the endocardial ablation system 2, 2' of the present invention is relatively easy for a clinician to use compared to the extensive training required to manipulate a steerable catheter or other similar device.

Alternatively, the ablation electrode may embody other electrode forms to achieve particular desired results. For example, FIG. 16 depicts an embodiment of the present invention in which a ball electrode 8' is integrated with the distal section 18 of the catheter 4. A catheter 4 according to the present invention incorporating a ball electrode 8' can similarly be manipulated by the wire rail systems of the present invention to ablate tissue 52 and create a lesion 54. Different ablation electrodes in addition to the brush electrode 8 and ball electrode 8' including, for example, virtual electrodes, may also be used depending upon the application or ablation effect desired. However, the advantages of the wire rail of the endocardial ablation system of the present invention for maintaining tissue contact are applicable regardless of the electrode chosen for use.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. An ablation system for ablating a surface of endocardial tissue, the system comprising
   a catheter;
   an ablation electrode positioned at a distal end of the catheter;
   a sheath defining a main lumen sized to receive the catheter within the main lumen and introduce the catheter into a cardiac cavity;
   a wire rail received within at least a portion of the sheath, the wire rail having a proximal first end and a distal second end, the second end being connected with the catheter proximal and adjacent to the ablation electrode,
   wherein the wire rail is wrapped around a distal end of the sheath, a first segment of the wire rail extending along an outer surface of the sheath, and a second segment of the wire rail extending along an inner surface of the sheath, and
   wherein pulling on the proximal first end of the wire rail causes relative sliding motion between the catheter and the sheath to extend the catheter from the sheath.

2. The system of claim 1, wherein the wire rail is fixed to a wall of the catheter.

3. The system of claim 1, wherein the ablation electrode comprises a brush tip.

4. The system of claim 1, wherein the sheath further defines a recessed trough adjacent to a distal tip of the sheath for receiving a portion of the wire rail distal to the connection of the wire rail with the catheter.

5. The system of claim 1, wherein the sheath further defines a rail port proximal to a distal tip of the sheath and a portion of the wire rail passes through the rail port.

6. The system of claim 5, wherein a proximal portion of the wire rail proximal to the rail port is received within the main lumen of the sheath.

7. The system of claim 5, wherein
the sheath further defines a rail lumen;
the rail port defines a passage to the rail lumen; and
a proximal portion of the wire rail proximal to the rail port is received within the rail lumen of the sheath.

8. The system of claim 7, wherein the wire rail is fixed to a wall of the catheter.

9. The system of claim 5, wherein the sheath further comprises
   an entry portion;
   an anchor portion; and
   a spanning portion positioned distal and adjacent to the entry portion and proximal and adjacent to the anchor portion, wherein
   the rail port is defined within the entry portion;
   the entry portion is shaped to direct the sheath into the cardiac cavity;
   the spanning portion maintains a separation distance between the anchor portion and the entry portion; and
   the anchor portion is curved to orient a distal tip of the anchor portion toward the rail port.

10. The system of claim 9, wherein the sheath further comprises a shape memory member within the entry portion, the spanning portion, and the anchor portion for shaping each of the entry portion, the spanning portion, and the anchor portion within the cardiac cavity.

11. The system of claim 1, wherein the catheter further comprises
   a distal section of a first material hardness;
   a suspension section of a second material hardness; and
   a directional section of a third material hardness, the directional section proximal and adjacent to the distal section and distal and adjacent to the suspension section.

12. The system of claim 11, wherein the directional section further comprises a preset curve for orienting the distal section toward the surface of endocardial tissue.

13. The system of claim 11, wherein when the surface is trabecular,
   the suspension section acts as a suspension with respect to the distal section allowing the ablation electrode to maintain constant contact with the endocardial tissue while tracing the trabecular surface.

14. An ablation system for ablating a surface of endocardial tissue, the system comprising
   a catheter;
   an ablation electrode positioned at a distal end of the catheter;
   a sheath defining a main lumen sized to receive the catheter within the main lumen and introduce the catheter into a cardiac cavity;
   a wire rail received within at least a portion of the sheath and connected with the catheter proximal and adjacent to the ablation electrode,
   wherein the sheath further defines a recessed trough adjacent to a distal tip of the sheath for receiving a portion of the wire rail distal to the connection of the wire rail with the catheter.

15. An ablation system for ablating a surface of endocardial tissue, the system comprising
   a catheter;
   a brush electrode positioned at a distal end of the catheter;
   a sheath defining a main lumen, a rail port, and a rail lumen, wherein the sheath is sized to receive the catheter within the main lumen and introduce the catheter into a cardiac cavity; and
   the rail port is proximal to a distal end of the sheath; and
   a wire rail received within the rail lumen, wherein the wire rail extends from a proximal end of the sheath at a first end of the wire rail, the wire rail emerges from the rail port, a segment of the wire rail extending along an outer surface of the sheath, and wraps around a distal end of the sheath, a segment of the wire rail extending along an inner surface of the sheath, and the wire rail is fixed at a second end of the wire rail to the catheter proximal and adjacent to the brush electrode, whereby pulling on the first end of the wire rail extends the catheter from the sheath.

\* \* \* \* \*